US008900556B2

(12) United States Patent
Oxman et al.

(10) Patent No.: US 8,900,556 B2
(45) Date of Patent: Dec. 2, 2014

(54) HARDENABLE THERMALLY RESPONSIVE COMPOSITIONS

(75) Inventors: Joel D. Oxman, Minneapolis, MN (US); Mai T. Nguyen, Maplewood, MN (US); Sumita B. Mitra, West St. Paul, MN (US); Hoa T. Bui, Mendota Heights, MN (US); Jingwen Ma, Woodbury, MN (US); Jie J. Liu, Woodbury, MN (US); Mahfuza B. Ali, Mendota Heights, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1610 days.

(21) Appl. No.: 11/745,212

(22) Filed: May 7, 2007

(65) Prior Publication Data

US 2007/0207094 A1      Sep. 6, 2007

Related U.S. Application Data

(63) Continuation of application No. 10/626,261, filed on Jul. 24, 2003, now abandoned.

(60) Provisional application No. 60/443,970, filed on Jan. 30, 2003.

(51) Int. Cl.
*A61K 6/00* (2006.01)
*A61K 6/083* (2006.01)
*A61K 31/765* (2006.01)
*A61K 6/087* (2006.01)

(52) U.S. Cl.
CPC ............... *A61K 6/083* (2013.01); *A61K 31/765* (2013.01); *A61K 6/0835* (2013.01); *A61K 6/087* (2013.01)
USPC ............................................. 424/49; 424/423

(58) Field of Classification Search
USPC .................................................... 424/49, 423
See application file for complete search history.

(56) References Cited

U.S. PATENT DOCUMENTS

| 3,786,116 A | 1/1974 | Milkovich et al. |
| 3,842,059 A | 10/1974 | Milkovich et al. |
| 4,018,732 A | 4/1977 | Lakshmanan |
| 4,071,424 A | 1/1978 | Dart et al. |
| 4,188,373 A * | 2/1980 | Krezanoski .................. 514/20.8 |
| 4,659,572 A | 4/1987 | Murray |
| 4,693,935 A | 9/1987 | Mazurek |
| 4,732,930 A | 3/1988 | Tanaka et al. |
| 4,871,786 A | 10/1989 | Aasen et al. |
| 5,063,257 A | 11/1991 | Akahane et al. |
| 5,130,347 A | 7/1992 | Mitra |
| 5,152,758 A | 10/1992 | Kaetsu et al. |
| 5,154,762 A | 10/1992 | Mitra et al. |
| 5,252,318 A | 10/1993 | Joshi et al. |
| 5,262,055 A | 11/1993 | Bae et al. |
| 5,346,703 A * | 9/1994 | Viegas et al. .................. 424/486 |
| 5,410,016 A | 4/1995 | Hubbell et al. |
| 5,429,826 A | 7/1995 | Nair et al. |
| 5,468,477 A | 11/1995 | Kumar et al. |
| 5,501,727 A | 3/1996 | Wang et al. |
| 5,546,676 A | 8/1996 | Palazzotto et al. |
| 5,580,929 A | 12/1996 | Tanaka et al. |
| 5,607,663 A | 3/1997 | Rozzi et al. |
| 5,612,052 A | 3/1997 | Shalaby |
| 5,662,887 A | 9/1997 | Rozzi et al. |
| 5,725,882 A | 3/1998 | Kumar et al. |
| 5,866,630 A | 2/1999 | Mitra et al. |
| 5,876,208 A | 3/1999 | Mitra et al. |
| 5,888,491 A | 3/1999 | Mitra et al. |
| 5,922,786 A | 7/1999 | Mitra et al. |
| 5,929,214 A | 7/1999 | Peters et al. |
| 5,939,485 A | 8/1999 | Bromberg et al. |
| 5,942,209 A | 8/1999 | Leavitt et al. |
| 5,976,648 A | 11/1999 | Li et al. |
| 6,018,033 A | 1/2000 | Chen et al. |
| 6,030,634 A | 2/2000 | Wu et al. |
| 6,060,582 A | 5/2000 | Hubbell et al. |
| 6,083,421 A | 7/2000 | Huang et al. |
| 6,121,341 A | 9/2000 | Sawhney et al. |
| 6,123,667 A | 9/2000 | Poff et al. |
| 6,136,885 A | 10/2000 | Rusin et al. |
| 6,162,241 A | 12/2000 | Coury et al. |
| 6,177,095 B1 | 1/2001 | Sawhney et al. |
| 6,201,065 B1 | 3/2001 | Pathak et al. |
| 6,217,894 B1 | 4/2001 | Sawhney et al. |
| 6,312,666 B1 | 11/2001 | Oxman et al. |
| 6,312,667 B1 | 11/2001 | Trom et al. |

(Continued)

FOREIGN PATENT DOCUMENTS

| EP | 0 173 567 | 3/1986 |
| EP | 0 363 095 | 4/1990 |
| EP | 0510211 | 1/1992 |
| EP | 1 004 293 | 5/2000 |
| EP | 1 266 570 | 12/2002 |
| JP | 58-099406 | 6/1983 |
| JP | 2-164807 | 6/1990 |
| JP | 2 229 443 | 9/1990 |
| JP | 04-041423 | 2/1992 |
| JP | 04-173713 | 6/1992 |

(Continued)

OTHER PUBLICATIONS

U.S. Appl. No. 10/626,142, filed Jul. 24, 2003, Mitra et al.

(Continued)

*Primary Examiner* — Frederick Krass
*Assistant Examiner* — Tracy Liu
(74) *Attorney, Agent, or Firm* — 3M Innovative Properties Company; Qiang Han

(57) ABSTRACT

Thermally responsive compositions that include a thermally responsive viscosity modifier, a polymerizable component, and water are provided. The compositions, which optionally may be hardened, are useful for application to a surface of a body.

27 Claims, 6 Drawing Sheets

(56) References Cited

U.S. PATENT DOCUMENTS

| | | |
|---|---|---|
| 6,312,668 B2 | 11/2001 | Mitra et al. |
| 6,316,011 B1 | 11/2001 | Ron et al. |
| 6,387,977 B1 | 5/2002 | Sawhney et al. |
| 6,410,645 B1 | 6/2002 | Pathak et al. |
| 6,419,906 B1 | 7/2002 | Xu et al. |
| 6,497,729 B1 | 12/2002 | Moussy et al. |
| 6,538,089 B1 | 3/2003 | Samra et al. |
| 6,616,946 B1 | 9/2003 | Meier et al. |
| 6,620,405 B2 | 9/2003 | Oxman et al. |
| 6,765,038 B2 | 7/2004 | Mitra |
| 6,982,288 B2 | 1/2006 | Mitra et al. |
| 7,025,950 B2 | 4/2006 | Majeti et al. |
| 7,173,074 B2 | 2/2007 | Mitra et al. |
| 7,223,826 B2 | 5/2007 | Ali et al. |
| 2002/0197214 A1 | 12/2002 | Bublewitz et al. |
| 2003/0044455 A1 | 3/2003 | Kazakov et al. |
| 2004/0001892 A1 | 1/2004 | Healy et al. |
| 2004/0007051 A1 | 1/2004 | Bashir et al. |
| 2004/0120901 A1 | 6/2004 | Wu et al. |
| 2004/0122126 A1 | 6/2004 | Wu et al. |
| 2004/0151691 A1 | 8/2004 | Oxman et al. |
| 2007/0043141 A1 | 2/2007 | Wu et al. |

FOREIGN PATENT DOCUMENTS

| | | |
|---|---|---|
| JP | 10-298046 | 10/1998 |
| JP | 11-502552 | 3/1999 |
| JP | 11-507672 | 7/1999 |
| JP | 3 101 714 | 10/2000 |
| JP | 2000319304 | 11/2000 |
| JP | 05-507928 | 3/2005 |
| WO | WO 93/17669 | 9/1993 |
| WO | WO 93/23009 | 11/1993 |
| WO | WO 95/24430 | 9/1995 |
| WO | WO 96/29370 | 9/1996 |
| WO | WO 97/00065 | 1/1997 |
| WO | WO 99/32152 | 7/1999 |
| WO | WO 00/00222 | 1/2000 |
| WO | WO 00/28946 | 5/2000 |
| WO | WO 00/44800 | 8/2000 |
| WO | WO 01/17574 | 3/2001 |
| WO | WO 01/30873 | 5/2001 |
| WO | WO 01/76549 | 10/2001 |
| WO | WO 03/094877 | 11/2003 |
| WO | WO 2004/069278 | 8/2004 |

OTHER PUBLICATIONS

Hoffman et al., "Thermally Reversible Hydrogels: II. Delivery and Selective Removal of Substances From Aqueous Solutions," Journal of Controlled Release, 4, Elsevier Science Publishers, Amsterdam, pp. 213-222 (1986).

Kawakami et al., "Silicone Macromers for Graft Polymer Synthesis," Polymer Journal, vol. 14, No. 11, pp. 913-917 (1982).

Kawakami et al., "Synthesis and Copolymerization of Polysilxoane Macromers," ACS Polymer Preprints 25(1), pp. 245-246 (1984).

Kawakami et al., "Synthesis of silicone graft polymers and a study of their surface active properties," Makromol. Chem., 185, pp. 9-18 (1984).

Lee et al., "pH-Thermoreversible Hydrogels. I. Synthesis and Swelling Behaviors of the (N-isopropylacrylamide-co-acrylamide-co-2-hydroxyethyl methacrylate) Copolymeric Hydrogels," Journal of Applied Polymer Science, vol. 71, John Wiley and Sons, Inc., pp. 221-231 (1999).

Lee et al., "Thermoreversible Hydrogels. XII. Effect of the Polymerization Conditions on the Swelling Behavior of the N-Isopropylacrylamide," Journal of Applied Polymer Science, vol. 78, John Wiley and Sons, Inc., pp. 1604-1611 (2000).

Lee et al., "Thermoreversible Hydrogels. XIV. Synthesis and Swelling Behavior of the (N-isopropylacrylamide-co-2-Hydroxyethyl methacrylate) Copolymeric Hydrogels," Journal of Applied Polymer Science, vol. 77, John Wiley and Sons, Inc., pp. 1769-1781 (2000).

Nathoo et al., "Comparative 3-Weed Clinical Tooth-Shade Evaluation of a Novel Liquid Whitening Gel Containing 18% Carbamide Peroxide and a Commercially Available Whitening Dentrifrice," A Supplement to Compendium of Continuing Education in Dentistry, vol. 23, No. 11 (Suppl. 1), Title page, letter from the editor, and pp. 12-17 (8 pp. total) (Nov. 2002).

Senel et al., "Thermoresponsive Isopropylacrylamide-Vinylpyrrolidone Copolymer by Radiation Polymerization," Journal of Applied Polymer Science, vol. 64, John Wiley and Sons, Inc., pp. 1775-1784 (1997).

Grayson, Editor, Kirk-Othmer Concise Encyclopedia of Chemical Technology, New York, NY 1985; title page, publisher's page, and pp. 648-649.

Carbonyl Compounds, University of Texas, www.geo.utexas.edu/courses.387E/PDF/carbonyl.pdf., pp. 1-7. Accessed Dec. 18, 2008.

Search Report for PCT/US03/40676.

Search Report for PCT/US03/41406.

Written Opinion for PCT/US03/41406.

Search Report for PCT/US03/40170.

"Ethylene Oxide/Propylene Oxide Block Copolymers," datasheet [online]. BASF The Chemical Company, [retrieved on Apr. 22, 2013]. Retrieved from the Internet<URL:http://worldaccount.basf.com/wa/NAFTA~en_GB/Catalog/ChemicalsNAFTA/pi/BASF/Subgroup/ethylene_oxide_propylene_oxide_block_Copolymers/polymers_pg/productgroup_top>; 3 pgs.

Karmarkar, A.B., "Poloxamers and their Applications," Pharmainfo.net [online], retrieved Apr. 16, 2013, Retrieved from the Internet: <URL:http://www.pharmainfo.net/pharma-student-magazine/poloxamers-and-their-applications-0> 50 pgs.

"Pluronic" datasheet [online] BASF—The Chemical Company, Florham Park, NJ, Copyright 2001-2013 [retrieved on Oct. 31, 2013]. Retrieved from the Internet:<URL:http://worldaccount.basf.com/wa/NAFTA/Catalog/ChemicalsNAFTA/pi/BASF/Brand/pluronic?view—Print>; 2 pgs.

\* cited by examiner

HARDENABLE THERMALLY RESPONSIVE COMPOSITIONS

CROSS REFERENCE TO RELATED APPLICATIONS

This application is a continuation of U.S. application Ser. No. 10/626,261, filed Jul. 24, 2003, now abandoned, which claims the benefit of U.S. Provisional Application No. 60/443,970, filed Jan. 30, 2003.

BACKGROUND

Thermally reversible gel compositions including a thermally responsive viscosity modifier work well for applications in environments where the temperature is generally higher than the ambient or pre-treatment temperature of the composition. Such compositions can be of low viscosity at ambient temperature, but substantially increase in viscosity or thicken to a thickened, semi-solid, or gel-like composition in the higher temperature environment (e.g., an oral environment). The use of compositions including thermally responsive viscosity modifiers has been reported for use in applications including, for example, dental whitening (e.g., U.S. Pat. No. 6,312,666 (Oxman et al.)) and dental etching (e.g., U.S. Pat. No. 6,312,667 (Trom et al.)).

What is needed are other thermally responsive compositions with desirable properties after application to a surface.

SUMMARY

In one aspect, the present invention provides a thermally responsive composition including: a thermally responsive viscosity modifier; a polymerizable component different than the modifier; and water. Preferably the thermally responsive viscosity modifier includes a poly(oxyalkylene) polymer that optionally includes a reactive group. Optionally, the composition is a dental composition suitable for use in the oral environment, with the composition being in the form of a dispersion, suspension, emulsion, or solution. Optionally, the composition is a medical composition suitable for use in or on the body.

In another embodiment, the present invention provides a method of treating a surface. The method includes: applying a thermally responsive composition in a low viscosity state at a pre-treatment temperature to the surface, the composition including a thermally responsive viscosity modifier, a polymerizable component different than the modifier, and water; and allowing the composition to warm to a treatment temperature and increase in viscosity to a highly viscous state.

In another aspect, the present invention provides a method of hardening a composition on a surface. The method includes: applying a thermally responsive composition in a low viscosity state at a pre-treatment temperature to the surface, the composition including a thermally responsive viscosity modifier, a polymerizable component different than the modifier, and water; allowing the composition to warm to a treatment temperature and increase in viscosity to a highly viscous state; and inducing the polymerizable component to polymerize.

In another aspect, the present invention provides a method of treating an oral surface of a body. The method includes: applying a thermally responsive composition in a low viscosity state at a pre-treatment temperature to the oral surface, the composition including a thermally responsive viscosity modifier, a polymerizable component, and water; and allowing the composition to warm to a treatment temperature and increase in viscosity to a highly viscous state.

In another aspect, the present invention provides a method of hardening a composition on an oral surface of a body. The method includes: applying a thermally responsive composition in a low viscosity state at a pre-treatment temperature to the oral surface, the composition including a thermally responsive viscosity modifier, a polymerizable component, and water; allowing the composition to warm to a treatment temperature and increase in viscosity to a highly viscous state; and inducing the polymerizable component to polymerize.

In another aspect, the present invention provides a method of making a thermally responsive viscosity modifier. The method includes reacting a hydroxy-terminated poly(oxyalkylene) polymer with an isocyanate-functional (meth)acrylate or a vinyl azlactone.

In another aspect, the present invention provides a thermally responsive viscosity modifier, and compositions thereof. The thermally responsive modifier includes a poly(oxyalkylene) polymer including at least one $CH_2=C(R)C(O)OCH_2CH_2NHC(O)O-$ group on an end of the poly(oxyalkylene) polymer, wherein R represents H or $CH_3$.

In another aspect, the present invention provides a thermally responsive viscosity modifier, and compositions thereof. The thermally responsive viscosity modifier includes a poly(oxyalkylene) polymer including at least one $CH_2=CHC(O)NHC(CH_3)_2C(O)O-$ group on an end of the poly(oxyalkylene) polymer.

In some embodiments of the present invention, the compositions and methods of the present invention provide hardenable compositions (e.g., hardenable gels). Hardenable compositions can offer advantages over unhardenable thermally reversible compositions. Advantages after hardening can include, for example, dimensional stability, thermal stability, improved stability to liquids, improved adhesion, and the potential for sustained release of incorporated additives (e.g., dental additives).

DEFINITIONS

As used herein, "thermally responsive" refers to the occurrence of a change in a physical property in response to a change in temperature.

As used herein, "thermally responsive viscosity modifier" means a material that may be incorporated into a composition to provide the composition the capability of substantially changing in viscosity (including a phase change, e.g., a single liquid phase to separate into separate liquid-liquid phases or liquid-solid phases) in response to a change in temperature.

As used herein, a "reactive" group is a group that can react under selected conditions (e.g., in the presence of free radicals or under condensation reaction conditions) with another reactive group or another component (e.g., a crosslinker or a compound with condensation reaction sites). For example, in a polymer that includes a reactive group, the reactive group can react with another reactive group and/or another component to form crosslinks through dimerization, oligomerization, and/or polymerization reactions.

As used herein, "hardenable" refers to a material that can be "hardened." As used herein, "harden" is meant to encompass processes including, for example, crosslinking, dimerization, oligomerization, and/or polymerization reactions.

As used herein, "(meth)acryl" is an abbreviation intended to refer collectively to "acryl" and/or "methacryl."

As used herein, "a," "at least one," and "one or more" are used interchangeably.

As used herein, the recitations of numerical ranges by endpoints include all numbers subsumed within that range (e.g., 1 to 5 includes, for example, 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS

Figure 1:
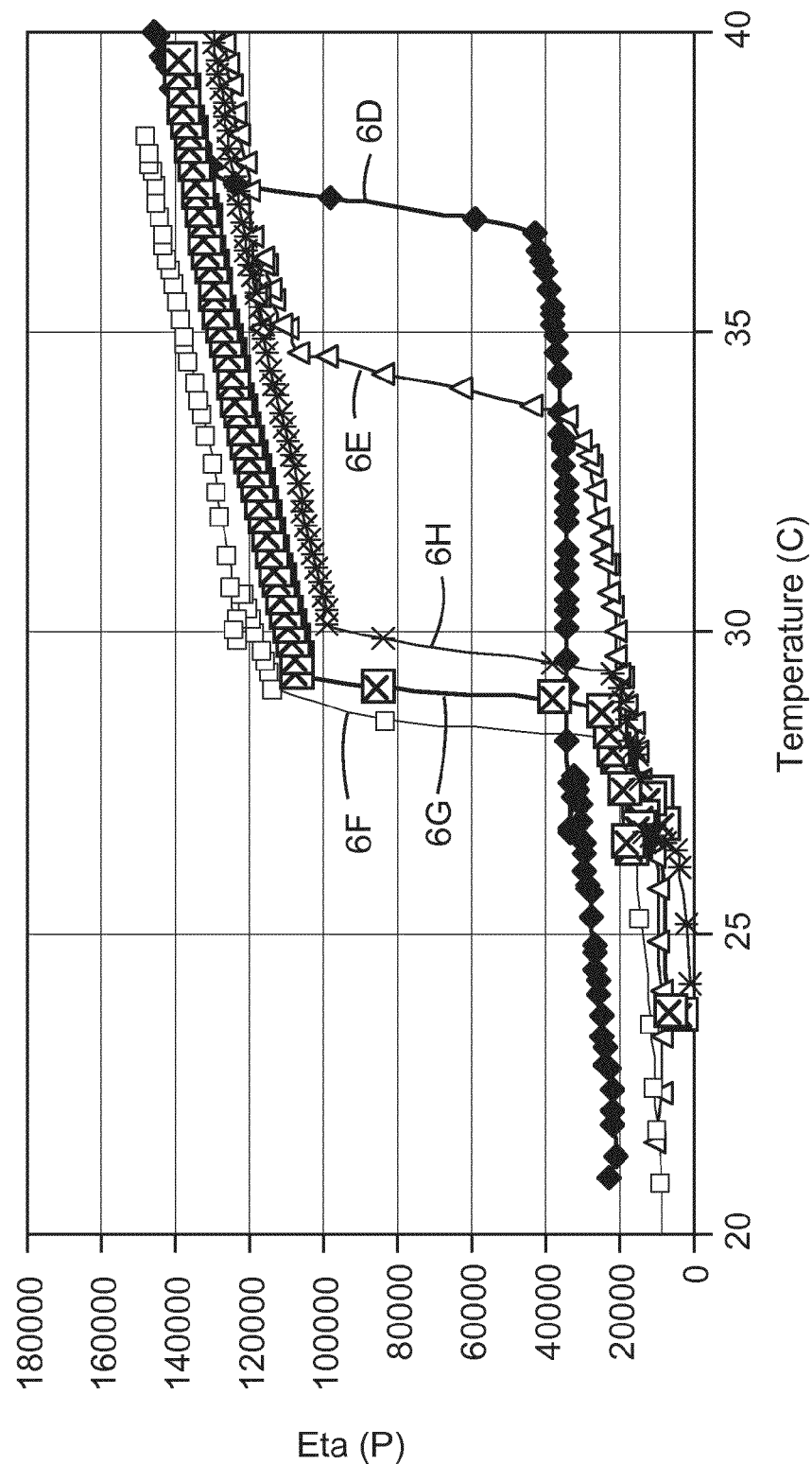
FIG. 1 is an illustration of plots of viscosity (Poise, y-axis) vs. temperature (° C., x-axis) generated using a Rheological Dynamic Analyzer (RDA, Model RDA II) for compositions including thermally responsive viscosity modifiers, polymerizable components, and water as defined in Table 1.

The present invention provides a thermally responsive composition. Such compositions are typically in a low viscosity state at a pre-treatment temperature prior to application onto a target site (e.g., a surface of a body), but typically become highly viscous (e.g., thick and controllable) at the target site. Once properly applied to the target site, the composition may optionally be hardened to provide a semi-permanent or permanent gel. These compositions are generally easily dispensed, applied, and manipulated when handled by the user, and are generally easily controlled upon application to the target site. Because the composition typically has a low viscosity (e.g., a free-flowing fluid state) initially at a pre-treatment temperature, it generally requires, for example, lower syringe extrusion forces to deliver the composition to the intended site. In addition, low viscosity compositions can provide the ability to spray a fine mist or aerosol to a relatively large surface area (e.g., an oral cavity), typically allowing subsequent long term retention upon gellation on the warm target site. This can allow the user the freedom to select a dispenser or applicator from an array of systems that are incapable of delivering high viscosity materials. In addition, production of low viscosity compositions may allow for easier processing and greater uniformity and consistency.

Thermally responsive compositions of the present invention are generally suitable for use in or on living tissues where a composition having a pre-treatment temperature at or lower than ambient (e.g., room temperature) is applied to hard and/or soft tissue that is near or at oral temperature (e.g., 30° C. to 39° C.). Optionally, the composition is a dental composition suitable for use in the oral environment, with the composition being in the form of a dispersion, suspension, emulsion, or solution. Optionally, the composition is a medical composition suitable for use in or on the body.

The ability to harden (e.g., with light) the thermally responsive composition in vivo can provide materials that exhibit enhanced physical properties and the advantage of not reverting to a fluid state upon cooling or simple aqueous dilution. Moreover, many of the problems of formulation, handling, delivery, and application of viscous compositions may be overcome, since the compositions of the present invention may be free-flowing liquids prior to treatment.

In a preferred embodiment of the invention, the initial viscosity of the unhardened composition at the pretreatment temperature may be low enough such that the composition is in a liquid state. Subsequently, upon exposure to treatment temperature (e.g., a temperature at or near oral temperature), the viscosity can increase to thicken the composition. A viscosity increase in the range of 5-fold, 10-fold, or even 100-fold or more can be experienced when the initial viscosity is such that the composition is a liquid. Thus, for example, a composition in a liquid state may have a viscosity of 0-7000 poise. In response to an increase in temperature, the viscosity of the composition can increase to at least 10,000 poise. Upon lowering the temperature, the unhardened composition preferably has the ability to reverse its viscosity and return to the flow properties of a liquid.

The pre-treatment temperature is the temperature at which the composition is subjected to prior to application or treatment. The pretreatment temperature is preferably at least 5° C. and more preferably at least 20° C. The pretreatment temperature is preferably at most 29° C. and more preferably at most 25° C. However, there may be certain instances where the temperature may be outside this range. A pre-treatment temperature of at least 20° C. allows the composition to be easily stored at ambient or room temperature. A pre-treatment temperature of at most 25° C. allows the composition to be easily stored at ambient or room temperature. However, the compositions of the invention can also be stored at lower, refrigerated pre-treatment temperatures of 5° C. to 10° C. to provide improved stability and shelf life. Preferably a refrigerated pretreatment temperature is at least 5° C. Preferably a refrigerated pretreatment temperature is at most 10° C. The treatment temperature is the temperature at which the composition is exposed to during application. The treatment temperature can be at or near body temperature. Preferably the treatment temperature is at least 30° C. Preferably the treatment temperature is at most 39° C.

Thermally responsive compositions of the present invention include a thermally responsive viscosity modifier, a polymerizable component, and water. Preferably the compositions also include an initiator system (e.g., one or more initiators).

Compositions of the present invention may be prepared as a single part liquid or gel by combining the above components. For example, the thermally responsive viscosity modifier and polymerizable component may be added to the water and mixed at the desired temperature (e.g., room temperature). Alternatively, compositions of the present invention may be prepared as multiple part liquids and/or gels that are mixed prior to delivery to the tissue. Such multiple part systems may provide shelf stability that may not exist in single part compositions including, for example, compositions including an initiator system based on two-component redox chemistry, and compositions including an additive that is incompatible with other materials in the composition.

Thermally responsive compositions of the present invention preferably include at least 30% by weight of water, and more preferably at least 40% by weight of water, based on the total weight of the thermally responsive composition. Thermally responsive compositions of the present invention preferably include at most 90% by weight of water, and more preferably at most 80% by weight of water, based on the total weight of the thermally responsive composition. Water is preferably purified by methods including, for example, distillation, filtration, and ion-exchange processes. In addition to water, compositions of the present invention may optionally include a solvent. Useful solvents include, for example, polyols (e.g., propylene glycol, poly(ethylene glycol), and glycerin). Preferably the solvent is a water miscible solvent.

Polymerizable Component

The hardenable thermally responsive compositions of the present invention include a polymerizable component, thereby forming polymerizable compositions. Thermally responsive compositions of the present invention preferably include at least 1% by weight of the polymerizable component and more preferably at least 5% by weight of the polymerizable component, based on the total weight of the thermally responsive composition. Thermally responsive compositions of the present invention preferably include at most 60% by weight of the polymerizable component and more preferably at most 50% by weight of the polymerizable component, based on the total weight of the thermally responsive composition.

In certain embodiments, the compositions are photopolymerizable, i.e., the compositions contain a polymerizable component and a photoinitiator (i.e., a photoinitiator system) that upon irradiation with actinic radiation initiates the polymerization (or hardening) of the composition. Such photopolymerizable compositions are preferably free radically polymerizable.

In certain embodiments, the compositions are chemically polymerizable, i.e., the compositions contain a chemical initiator system that can polymerize, cure, or otherwise harden the composition without dependence on irradiation with actinic radiation. Such chemically polymerizable compositions are sometimes referred to as "self-cure" compositions and may include, for example, glass ionomer cements (e.g., conventional and resin-modified glass ionomer cements), redox cure systems, silane moieties capable of undergoing a condensation reaction (as described, for example, in U.S. Pat. No. 5,607,663 (Rozzi et al.), U.S. Pat. No. 5,662,887 (Rozzi et al.), U.S. Pat. No. 5,866,630 (Mitra et al.), U.S. Pat. No. 5,876,208 (Mitra et al.), U.S. Pat. No. 5,888,491 (Mitra et al.), and U.S. Pat. No. 6,312,668 (Mitra et al.)), and combinations thereof.

Ethylenically Unsaturated Compounds. Ethylenically unsaturated compounds include, for example, polymerizable monomers, polymerizable oligomers, polymerizable polymers, and combinations thereof. Preferably, the polymerizable component is free radically polymerizable. Optionally, the ethylenically unsaturated compound includes a plurality of polymerizable groups. Preferred monomers, oligomers, and polymers are those which are partially or fully water miscible.

Suitable polymerizable monomers and oligomers include, for example, poly(ethyleneglycol) dimethacrylate (PEGDMA), tetrahydrofurfural methacrylate, as well as hydroxylic functional monomers including, for example, 2-hydroxyethyl methacrylate (HEMA), glycidyl dimethacrylate (GDMA), and glycidyl monomethacrylate (GMMA). Hydrophobic monomers and oligomers including, for example, bis(glycidyl methacrylate) (bis-GMA), tri(ethyleneglycol) dimethacrylate (TEGDMA), and urethane dimethacrylate may also be utilized.

Suitable polymerizable polymers include, for example, partially or fully acrylate- or methacrylate-functionalized polymers including, for example, functionalized poly(acrylic acid) polymers, cellulosics, poly(vinylalcohol) polymers, poly(oxyethylene)-poly(oxypropylene) block copolymers, poly(ethyleneglycol) polymers, and the like.

Chemically Polymerizable Compositions. Chemically polymerizable compositions may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass. The glass ionomer cements may also include resin-modified glass ionomer ("RMGI") cements. Exemplary chemically polymerizable compositions are described, for example, in Applicants' Assignees' copending application Ser. No. 10/327,411, filed Dec. 20, 2002.

The chemically polymerizable compositions may include redox cure systems that include a polymerizable component (e.g., an ethylenically unsaturated polymerizable component) and redox agents. The redox agents may include an oxidizing agent and a reducing agent. Suitable polymerizable components, redox agents, optional acid-functional components, and optional fillers that are useful in the present invention are described in Applicants' Assignees' copending application Ser. Nos. 10/121,326 and 10/121,329, both filed Apr. 12, 2002. Alternatively, the redox agents may include a free-radical initiator system containing enzymes as disclosed in Applicants' Assignees' copending application Ser. No. 10/327,202, filed Dec. 20, 2002.

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently compatible with the thermally responsive composition (and preferably water-miscible) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethyla-niline; aromatic sulfinic salts, such as p-toluenesulfinic salts and benzenesulfinic salts; thioureas, such as 1-ethyl-2-thio-urea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in Applicants' Assignees' copending application Ser. No. 10/121,329, filed Apr. 12, 2002.

The reducing and oxidizing agents are present in amounts sufficient to permit an adequate free-radical reaction rate. This can be evaluated by combining all of the ingredients of the polymerizable composition except for any optional filler, and observing whether or not a hardened mass is obtained.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-immiscible encapsulant, the reducing and oxidizing agents can be combined with an FAS glass and water and maintained in a storage-stable state.

A redox cure system can be combined with other cure systems, e.g., with a glass ionomer cement and with a photopolymerizable composition such as described U.S. Pat. No. 5,154,762 (Mitra et al.).

The hardenable compositions that utilize a redox cure system can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the reducing agent is present in one part of the system, then the oxidizing agent is typically present in another part of the system. However, the reducing agent and oxidizing agent can be combined in the same part of the system through the use of the microencapsulation technique.

Thermally Responsive Viscosity Modifier

Thermally responsive compositions of the present invention preferably include at least 5% by weight of the thermally responsive viscosity modifier and more preferably at least 10% by weight of the thermally responsive viscosity modifier, based on the total weight of the thermally responsive composition. Thermally responsive compositions of the present invention preferably include at most 60% by weight of the thermally responsive viscosity modifier and more preferably at most 50% by weight of the thermally responsive viscosity modifier, based on the total weight of the thermally responsive composition.

Thermally responsive viscosity modifiers include, for example, poly(oxyalkylene) polymers, particularly the polymeric surfactants available under the trade designation PLURONIC from BASF Wyandotte (Wyandotte, Mich.). Other poly(oxyalkylene) polymers may also be useful as a thermally responsive viscosity modifiers. Preferably at least 50%, and more preferably at least 70%, of the oxyalkylene units in the polymer are oxyethylene units. Another class of suitable thermally responsive viscosity modifiers is poly(N-alkyl (meth)acrylamide) polymers including, for example, poly(N-isopropylacrylamide) prepared from the free radical polymerization of N-isopropylacrylamide as disclosed, for example, in Applicants' Assignees' copending application Ser. No. 10/626,341.

A preferred thermally responsive viscosity modifier in accordance with this invention includes a poly(oxyethylene)-poly(oxypropylene) block copolymer. Poly(oxyethylene)-poly(oxypropylene) block copolymers in which the number of oxyethylene units is at least 50% of the number of units in the total molecule, and the block copolymer having an average molecular weight of 1100 to 15,500 is particularly preferred. Preferably, the polymer includes 70% oxyethylene units, based on the total number of monomeric units in the copolymer. Preferably, the copolymer has an average molecular weight of 11,500. Exemplary theramlly reversible viscosity modifiers include, for example, compositions available under the trade designation PLURONIC F-127, F-68, and F-108 from BASF Wyandotte (Wyandotte, Mich.).

Poly(oxypropylene)-poly(oxyethylene) condensates that terminate in primary hydroxyl groups are available under the trade designation PLURONIC from BASF Wyandotte (Wyandotte, Mich.), and may be represented empirically by the formula: $HO(C_2H_4O)_a(C_3H_6O)_b(C_2H_4O)_cH$ where a and c are statistically equal. The concentration of the block copolymers is an important parameter and can be adjusted to provide the desired properties. By adjusting the concentration of the thermally responsive viscosity modifier based on other materials present in the composition, a desired liquid to semi-solid transition temperature above ambient temperature and below body temperature can be achieved. Thus, the selection of a concentration of the thermally responsive viscosity modifier in combination with other materials in the composition, will provide a liquid to semi-solid transition temperature in the desired range.

Optionally, the thermally responsive viscosity modifier may include a reactive group. For example, when the thermally responsive viscosity modifier is a poly(oxyalkylene) polymer, the polymer may include an ethylenically unsaturated group and/or an acidic group (e.g., a carboxylic acid group). Thermally responsive viscosity modifiers including an ethylenically unsaturated group can react, for example, in the presence of free radicals to form crosslinks through dimerization, oligomerization, and/or polymerization reactions. Thermally responsive viscosity modifiers including an acidic group can react, for example, in the presence of acid sensitive fillers to form a hardened glass ionomer cement.

Poly(oxyalkylene) polymers that include an ethylenically unsaturated group can be prepared by methods as disclosed, for example, in U.S. Pat. No. 6,201,065 (Paathak et al.). In brief, a hydroxy-terminated poly(oxyalkylene) polymer can be reacted with a moiety (e.g., acryloyl chloride; an isocyanate-functional (meth)acrylate such as 2-isocyantoethyl methacrylate; or a vinyl azlactone such as 4,4-dimethyl-2-vinyl-2-oxazolin-5-one) that results in the formation of at least one terminal ethylenically unsaturated group. Preferably, the ethylenically unsaturated group is an acrylate or methacrylate group. More preferably, at least one $CH_2=C(CH_3)C(O)OCH_2CH_2NHC(O)O-$ group or $CH_2=CHC(O)NHC(CH_3)_2C(O)O-$ group is attached to an end of the poly(oxyalkylene) polymer. Even more preferably a $CH_2=C(CH_3)C(O)OCH_2CH_2NHC(O)O-$ group or a $CH_2=CHC(O)NHC(CH_3)_2C(O)O-$ is attached to each end of the poly(oxyalkylene) polymer.

Poly(oxyalkylene) polymers that include an acidic group can be prepared by methods that are well known to one of skill in the art. Preferably, the acidic group is a carboxylic acid group. Suitable methods include, for example, the reaction of a hydroxy-terminated poly(oxyalkylene) polymer with a moiety (e.g., a cyclic anhydride or a haloalkanoic acid) to directly result in the formation of at least one terminal acidic group. Alternatively, a hydroxy-terminated poly(oxyalkylene) polymer can be reacted with a moiety (e.g., a haloalkanoic ester) to result in the formation of at least one terminal ester group that can then be hydrolyzed to form at least one terminal acidic group. Alternatively, a hydroxy-terminated poly(oxyalkylene) polymer can be oxidized to form at least one terminal acidic group.

Initiator System

Thermally responsive compositions of the present invention preferably include an initiator system or catalyst that enables the composition to be hardened. For example, visible and/or near-infrared photoinitiator systems may be used to initiate photopolymerization in compositions including free-radically polymerizable components. For example, a monomer can be combined with a three component or ternary photoinitiator system including a sensitizer, an electron donor, and an iodonium salt as disclosed, for example, in U.S. Pat. No. 5,545,676 (Palazzotto et al.). Alternatively, the composition may include a binary initiator system including a sensitizer (e.g., camphorquinone) and an electron donor (e.g., a secondary or a tertiary alkyl amine compound as disclosed, for example, in U.S. Pat. No. 4,071,424 (Dart et al.)).

Another class of useful photoinitiators includes acylphosphine oxides, as disclosed in European Pat. Publ. No. 173,567 (Ying). Such acylphosphine oxides are of the general formula $(R)_2P(=O)C(=O)-R^1$, wherein each R individually can be a hydrocarbyl group (e.g., alkyl, cycloalkyl, aryl, and aralkyl), which may be substituted with a halo-, alkyl- or alkoxy-group, or the two R groups may be joined to form a ring along with the phosphorous atom, and wherein $R^1$ is a hydrocarbyl group, an S—, O—, or N-containing five- or six-membered heterocyclic group, or a $-Z-C(=O)-P(=O)-(R)_2$ group, wherein Z represents a divalent hydrocarbyl group (e.g., alkylene or phenylene) having from 2 to 6 carbon atoms.

Preferred acylphosphine oxides useful in the invention are those in which the R and $R^1$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide available under the trade designation IRGACURE 819 from Ciba Specialty Chemicals (Tarrytown, N.Y.).

The use of redox catalysts including oxidants and reductants for inducing free radical polymerization in multi-component systems is also useful for generating hardened gels. A preferred mode of initiating the polymerization reaction uses oxidizing and reducing agents as a redox catalyst system. Various redox systems optionally including microencapsulated reducing and/or oxidizing agents are disclosed in U.S. Pat. No. 5,154,762 (Mitra et al.).

Preferably, the oxidizing agent reacts with or otherwise cooperates with the reducing agent to produce free radicals. The free radicals are capable of initiating polymerization of the ethylenically unsaturated moiety. The oxidizing and reducing agents preferably are sufficiently soluble and are present in an amount sufficient to permit an adequate free radical reaction rate as disclosed in U.S. Pat. No. 6,136,885 (Rusin et al.).

A preferred class of oxidizing agents includes persulfates (e.g., sodium, potassium, ammonium, and alkyl ammonium persulfates). Another preferred class of oxidizing agents includes peroxides or peroxide salts (e.g., hydrogen peroxide, benzoyl peroxide, and hydroperoxides including, for example cumene hydroperoxide, tert-butyl hydroperoxide, tert-amyl hydroperoxide, and 2,5-dihydroperoxy-2,5-dimethylhexane). Other preferred oxidizing agents include salts of cobalt (III) and iron (III), perboric acid and its salts, and salts of a permanganate anion. Combinations of any of the above mentioned oxidizing agents can also be used.

Preferred reducing agents include, for example, amines (e.g., aromatic amines), ascorbic acid, metal complexed ascorbic acid, cobalt (II) chloride, ferrous chloride, ferrous sulfate, hydrazine, hydroxylamine, oxalic acid, thiourea, and salts of dithionite, thiosulfate, benzene sulfinate, or sulfite anions.

If initiators are included in compositions of the present invention, the compositions preferably include at least 0.01% by weight of the initiator and more preferably at least 1% by weight of the initiator, based on the total weight of the composition. If initiators are included in compositions of the present invention, the compositions preferably include at most 10% by weight of the initiator and more preferably at most 5% by weight of the initiator, based on the total weight of the composition.

Additives

In some embodiments, compositions of the present invention include, or may optionally include, additives (e.g., medical additives for medical compositions that are suitable for use in or on the body, dental additives for dental compositions that are suitable for use in the oral environment). Exemplary additives include, for example, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, medicaments, indicators, dyes, pigments, wetting agents, surfactants, buffering agents, viscosity modifiers, thixotropes, fillers, polyols, antimicrobial agents, antifungal agents, stabilizers, agents for treating xerostomia, desensitizers, and combinations thereof. Preferably the additives are dental additives suitable for use in the oral environment.

Useful additives may be selected for specific applications as desired. For example, thermally responsive dental whitening compositions generally include a whitening agent. The whitening agent used in the present invention may be any material that has the effect of whitening teeth. Useful whitening agents include, for example, hypochlorites (e.g., sodium hypochlorite), peroxides, hydroperoxides, hydrogen peroxide, peracids (also known as peroxyacids), carbamide peroxide (i.e., the urea complex of hydrogen peroxide, $CO(NH_2)_2H_2O_2$, also known as urea hydrogen peroxide, hydrogen peroxide carbamide, or perhydrol-urea), and combinations thereof. The concentration of a whitening agent in the composition can vary depending upon its activity.

Thermally responsive compositions of the present invention may also include non-polymerizable polymers. Preferably, the non-polymerizable polymers are partially or fully miscible in an aqueous environment and include, for example, poly(acrylic acid) polymers, cellulosics, poly(vinylalcohol) polymers, poly(oxyethylene)-poly(oxypropylene) block copolymers, poly(ethyleneglycol) polymers, and combinations thereof.

Methods

Methods of the present invention provide for the treatment of a surface. In one embodiment, the treated surface is the surface (e.g., soft or hard tissue) of a body (e.g., animal or human). Hard tissues include, for example, bone, teeth, and the component parts of teeth (e.g., enamel, dentin, and cementum). Soft tissues include, for example, mucosa (e.g., tongue, gingiva, and throat).

Alternatively, the treated surface may be, for example, a substrate (e.g., a flexible film). Preferably the surface-treated substrate may be shaped or deformed. More preferably, the surface-treated substrate may be shaped or deformed by pressure from the surface of a body (e.g., a hand, a foot, a tooth). If only one surface of the substrate is treated, the pressure may be applied from either side of the substrate.

Compositions of the present invention may be delivered to the desired site by any method as desired. For example, the composition may be delivered directly onto the target site from a container or dispenser. Suitable containers or dispensers include, for example, bottles, vials, syringes, and tubes. The ability to delivery the composition as a bulk liquid from a needle tip or as a fine mist from an aerosol provides versatility in application. Alternatively, the composition can be delivered by using a brush, sponge, applicator, or swab to paint or coat the composition onto the target site. For some applications it may be desirable to apply the composition to larger areas. For those particular applications, the compositions may be delivered via spray or aerosol dispensers or by simply rinsing the entire target area (e.g., the oral cavity) with the liquid. Another alternative mode of delivery includes the use of a tray type dispenser.

Alternatively, the composition can be applied to a substrate, and the substrate having the composition thereon can be applied to the desired surface. Suitable substrates include, for example, polymeric films, paper, and woven and nonwoven sheets. The composition can also be applied to a brush, spatula, medical/dental instrument, or an applicator prior to application to the desired surface.

When the thermally responsive compositions of the present invention include two or more parts, the two or more parts are preferably mixed just prior to or during the application process. Suitable mixing devices include, for example, static mixing devices.

The composition is preferably allowed to stand on the surface of the target site long enough to provide the desired effect. The standing time will vary depending on the particular composition employed, the type of target site (e.g., tissue), the intended use, and the time available for carrying out the procedure. For many applications, the composition may be allowed to remain on the target site for an extended period of time.

Prior to hardening, thermally reversible compositions of the present invention can be readily removed from the target site by cooling the material below the liquid to semi-solid transition temperature, thus reversing the thickening effect. This can be accomplished with cool water or other physiologically compatible liquids. Alternatively, the concentrations of the components in the composition may be adjusted and diluted by adding water or other liquids. By adjusting the concentrations of the components, the transition temperature is correspondingly adjusted, and thus provides the user the ability to remove the composition even with warm solutions. Water or other liquids may be administered through a rinsing cup, squirt bottle, a liquid dispensing dental tool, or any other liquid dispensing device that can provide a liquid to the oral environment. Preferably, administering cool or cold water provides a significant decrease in viscosity. Alternatively, the composition may be brushed, wiped, or blown off.

Thermally responsive compositions of the present invention may be hardened by inducing the polymerizable component to polymerize. For example, when the polymerizable component is an ethylenically unsaturated compound, polymerization may be induced by the application of actinic radiation. Preferably the composition is irradiated with radiation having a wavelength of 400 to 1200 nanometers, and more preferably with visible radiation. Visible light sources include, for example, the sun, lasers, metal vapor (e.g., sodium and mercury) lamps, incandescent lamps, halogen lamps, mercury arc lamps, fluorescent room light, flashlights, light emitting diodes, tungsten halogen lamps, and xenon flash lamps.

Alternatively, when the polymerizable component is an ethylenically unsaturated compound, the composition may include two or more parts, with one part including an oxidizing agent, and another part including a reducing agent.

Upon exposure to treatment temperature (e.g., a temperature at or near oral temperature) and hardening, the viscosity of the composition can increase to thicken the composition. A viscosity increase in the range of 10-fold, 50-fold, or even 100-fold or more can be experienced when the initial viscosity is such that the composition is a liquid.

Once a composition of the present invention has been hardened, the composition is rendered thermally irreversible and is generally not readily removed by reducing temperature or diluting with water. However, the hardened composition can generally be removed by mechanical or chemical methods including, for example, brushing, wiping, scraping, and use of solvents (e.g., alcohols).

The substantial moisture content of the thermally reversible compositions of the present invention provides the ability to easily deliver or apply a gel-on-contact aqueous material that provides substantial hydration of tissues that are subject to dehydration. Compositions of the present invention may also be useful for applications including, for example, tissue adhesives and sealants for surgical and medical applications;

treatment of periodontal disease; treatment of gingivitis, teeth whitening, caries reduction gels; oral coatings (with/without local anesthetics) for hard and soft tissues; dermal and subdermal delivery of drugs, treatment of sensitivity, treatment of halitosis, and treatment of xerostomia.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Rheological Test Method

The theological properties of selected samples were measured with a Rheological Dynamic Analyzer (RDA) (Model RDA II, Rheometric Scientific, Piscataway, N.J.) following manufacturer's recommended procedure. Samples were tested as 25-mm diameter discs using a 1-mm gap distance and a temperature range of 20° C. to 40° C. A general objective of the measurements was to find thermoreversible compositions that transitioned from a low-viscosity liquid state to a viscous gel state (i.e., "gellation") at 30° C.

Fluoride Release Test Method

The fluoride release over time of test compositions was measured with a fluoride selective electrode according to standard methodology and with the following apparatus set-up. Fifty-ml glass vials containing cylindrical Pyrex molds (14-mm in diameter and 5-mm in length) and a small magnetic stirrer were placed in a 37° C. oven and the mass of the empty molds recorded. Aliquots of different test compositions were syringed fully into the mold cavities and the mass of the filled molds recorded. Water (25 ml) at 37° C. was added to the different vials such that the molds were entirely covered by the water. Samples to be light cured were then exposed to a dental curing light for 60 seconds. The vials were placed on a heated magnetic stirring plate at a speed level 3 and heated to maintain the vials at 37° C. The fluoride content was determined using the fluoride selective electrode at several times over the course of 75 minutes and the samples then stored in a 37° C.-oven for 1440 minutes (24 hours). After storage, a final fluoride measurement was taken, allowing at least 10 minutes for the reading to stabilize. The resulting data (parts per million (ppm) fluoride ion) were normalized so that the fluoride content at 24 hours was equivalent to the total fluoride contained in the test compositions.

Compressive Strength (CS) Test Method

Compressive strength was evaluated by first injecting a mixed cement sample into a glass tube having a 4-mm inner diameter. The ends of the glass tube were plugged with silicone plugs. The filled tubes were subjected to 0.275 megapascal (MPa) pressure for 5 minutes, placed in a chamber at 37° C. and greater than 90% relative humidity (RH) and allowed to stand for 1 hour. The cured sample was next placed in 37° C. water for 1 day, and then cut to a length of 8 mm. Compressive strength was determined according to ISO Standard 7489 using an INSTRON universal tester (Instron Corp., Canton, Mass.) operated at a crosshead speed of 1 millimeter per minute (mm/min).

Diametral Tensile Strength (DTS) Test Method

Diametral tensile strength was measured using the above-described CS procedure, but using samples cut to a length of 2 mm.

Abbreviations/Definitions

| | |
|---|---|
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity $\rho$ = 4.64. |
| IEM | 2-Isocyanatoethyl methacrylate (Sigma-Aldrich, St. Louis, MO) |
| AA:ITA:IEM | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. |
| HEMA | 2-Hydroxyethyl methacrylate (Sigma-Aldrich) |
| PEG 400 | Polyethylene glycol, MW = approximately 400 (Sigma-Aldrich) |
| PEGDMA 400 | Polyethyleneglycol dimethacrylate (Sartomer, Exton, PA) |
| TEGDMA | Triethyleneglycol dimethacrylate (Sartomer, Exton, PA) |
| PLURONIC F68 | Polyoxyethylene-polyoxypropylene block copolymer (BASF Wyandotte, Wyandotte, MI) |
| PLURONIC F127 | Polyoxyethylene-polyoxypropylene block copolymer (BASF Wyandotte, Wyandotte, MI) |
| IRGACURE 819 | Phosphine oxide photoinitiator (Ciba Specialty Chemicals Corp., Terrytown, NY) |
| CPQ | Camphorquinone (Sigma-Aldrich) |
| EDMAB | Ethyl 4-(N,N-dimethylamino)benzoate (Sigma-Aldrich) |
| DPIHFP | Diphenyliodonium hexafluorophosphate (Johnson Matthey, Alpha Aesar Division, Ward Hill, NJ) |
| BHT | 2,6-Di-tert-butyl-4-methylphenol (Sigma-Aldrich) |
| DBU | 1,8-Diazabicyclo(5.4.0)undec-7-ene (Sigma-Aldrich) |
| $TMA-BF_4$ | Trimethylammoniumethyl methacrylate tetrafluoroborate (Prepared as described for SM-1) |
| Tetracycline HCl | Tetracycline hydrochloride (Sigma-Aldrich) |
| Lidocaine HCl | Lidocaine hydrochloride (Sigma-Aldrich) |
| VDMA | Vinyl dimethyl azlactone (4,4-dimethyl-2-vinyl-2-oxazolin-5-one; Group SNPE, Strasbourg, France) |

Starting Materials

SM-1

Synthesis of Trimethylammoniumethyl Methacrylate Tetrafluoroborate ($TMA-BF_4$)

A three-necked flask fitted with a mechanical stirrer, a dropping funnel and a condenser was charged with 80 parts of sodium tetrafluoroborate (Alfa Aesar Inorganics, Ward Hill, Mass.) and 130 parts of DI water. The mixture was stirred for 15 minutes and a clear solution was obtained. From the dropping funnel a solution of 202.4 parts of dimethylaminoethyl methacrylate-methyl chloride (trimethylammoniumethyl methacrylate chloride; CPS Company, CPS Company, Ciba, Crystal Lake, Ill.) and 80 parts of DI water was added slowly. A solid product immediately began to precipitate out. After the addition was complete, the mixture was stirred for 30 minutes and the solid isolated by filtration, washed with 30 parts of DI water, and dried under vacuum at 40° C. An NMR analysis of the solid product revealed the structure to be pure trimethylammoniumethyl methacrylate tetrafluoroborate.

Example 1

Thermoreversible (TR) Viscosity Modifiers +Polymerizable Components

PLURONIC F127 (12.24 parts), PLURONIC F68 (4.12 parts), and water (56.42 parts) were combined and thoroughly mixed in a vessel cooled by an ice bath (approximately 4° C.). To the resulting solution was added PEG 400 (10.16 parts), IA:ITA:IEM (3.4 parts), PEGDMA 400 (10.85 parts), TEGDMA (2.29 parts), and IRGACURE 819 (0.5 parts). The resulting composition was mixed thoroughly at room temperature (22° C.) and the resulting solution designated Example 1.

An aliquot of Example 1 was transferred to a syringe and delivered through the needle tip of the syringe onto a sheet of polyester film heated to 37° C. The liquid aliquot immediately transformed into a viscous, immobile (i.e., non-flowing) gel on the polyester film. Upon cooling the polyester film back to room temperature, the viscous gel was transformed back into a flowable liquid state (i.e., "thermoreversible"). In another experiment, the viscous gel (at 37° C.) was directly exposed to a dental curing light and thereby cured to a hardened material that was unchanged when cooled back to room temperature (i.e., not "thermoreversible"). The hardened material showed no significant change in appearance when stored for 15 days in 5 ml of a 0.9% saline solution at 37° C.

Example 2

TR Viscosity Modifiers+Polymerizable Components+Fluoride Source

PLURONIC F127 (16 parts), PLURONIC F68 (8 parts), and water (47 parts) were combined and thoroughly mixed in a vessel cooled by an ice bath (approximately 4° C.). To the resulting solution was added PEG 400 (10 parts), IA:ITA:IEM (2 parts), PEGDMA 400 (10 parts), TEGDMA (2 parts), TMA-BF$_4$ (5 parts), and IRGACURE 819 (0.2 parts). The resulting composition was mixed thoroughly at the ice bath temperature and the resulting solution designated Example 2. The solution thickened (i.e., became more viscous) at room temperature and transformed back to its original lower viscosity liquid solution when cooled back to 2° C. to 5° C.

A cooled aliquot of Example 2 was transferred to a syringe and delivered through the needle tip of the syringe onto a sheet of polyester film heated to 37° C. The liquid aliquot immediately transformed into a viscous, immobile gel on the polyester film. Upon cooling the polyester film back to 2° C. to 5° C., the viscous gel was transformed back into a flowable liquid state. In another experiment, the viscous gel (at 37° C.) was directly exposed to a dental curing light and thereby cured to a hardened material that was unchanged when cooled back to room temperature or below. The hardened material showed no significant change in appearance when stored for 10 days in 5 ml of a 0.9% saline solution at 37° C.

Example 3

TR Viscosity Modifiers+Polymerizable Components+Tetracycline HCl

PLURONIC F127 (13 parts), PLURONIC F68 (4 parts), and water (53 parts) were combined and thoroughly mixed in a vessel cooled by an ice bath (approximately 4° C.). To the resulting solution was added PEG 400 (10 parts), IA:ITA:IEM (2 parts), PEGDMA 400 (10 parts), TEGDMA (2 parts), Sucrose (5 parts), Tetracycline HCl (1 part), and IRGACURE 819 (0.2 parts). The resulting composition was mixed thoroughly at room temperature and the resulting solution designated Example 3.

An aliquot of Example 3 was transferred to a syringe and delivered through the needle tip of the syringe onto a sheet of polyester film heated to 37° C. The liquid aliquot immediately transformed into a viscous, immobile gel on the polyester film. Upon cooling the polyester film back to room temperature, the viscous gel was transformed back into a flowable liquid state. In another experiment, the viscous gel (at 37° C.) was directly exposed to a dental curing light and thereby cured to a hardened material that was unchanged when cooled back to room temperature. The hardened material showed no significant change in appearance when stored for 12 days in 5 ml of a 0.9% saline solution at 37° C.

Example 4

TR Viscosity Modifiers+Polymerizable Components+Lidocaine HCl

Example 4 solution was prepared as described for Example 3, except that 49 parts of water was used and Lidocaine HCl (10 parts) was used in place of sucrose and Tetracycline HCl.

An aliquot of Example 4 was transferred to a syringe and delivered through the needle tip of the syringe onto a sheet of polyester film heated to 37° C. The liquid aliquot immediately transformed into a viscous, immobile gel on the polyester film. Upon cooling the polyester film back to room temperature, the viscous gel was transformed back into a flowable liquid state. In another experiment, the viscous gel (at 37° C.) was directly exposed to a dental curing light and thereby cured to a hardened material that was unchanged when cooled back to room temperature. The hardened material showed no significant change in appearance when stored for 12 days in 5 ml of a 0.9% saline solution at 37° C.

Example 5

TR Viscosity Modifiers+Polymerizable Components+Fluoride/Tetracycline

Example 5 solution was prepared as described for Example 3, except that 48 parts of water was used and TMA-BF$_4$ (5 parts) was additionally added to the composition.

An aliquot of Example 5 was transferred to a syringe and delivered through the needle tip of the syringe onto a sheet of polyester film heated to 37° C. The liquid aliquot immediately transformed into a viscous, immobile gel on the polyester film. Upon cooling the polyester film back to room temperature, the viscous gel was transformed back into a flowable liquid state. In another experiment, the viscous gel (at 37° C.) was directly exposed to a dental curing light and thereby cured to a hardened material that was unchanged when cooled back to room temperature. The hardened material showed no significant change in appearance when stored for 12 days in 5 ml of a 0.9% saline solution at 37° C.

Examples 6A-6H

TR Viscosity Modifier+Polymerizable Components

PLURONIC F127 (9.1 parts), IA:ITA:IEM (36.4 parts), HEMA (9.1 parts), and water (45.5 parts) were transferred to a 250-ml plastic container and thoroughly mixed at room temperature. The resulting solution was designated Example 6A. Examples 6B-6H were prepared in a similar manner with the amounts of individual components shown in Table 1.

TABLE 1

Component Amounts for Examples 6A-6H

| | Amount (Parts) | | | | | | | |
|---|---|---|---|---|---|---|---|---|
| Component | 6A | 6B | 6C | 6D | 6E | 6F | 6G | 6H |
| Pluronic F127 | 9.1 | 13.0 | 20.0 | 25.0 | 25.9 | 27.3 | 27.0 | 26.6 |
| IA:ITA:IEM | 36.4 | 34.8 | 32.0 | 32.0 | 29.6 | 29.1 | 29.2 | 29.4 |
| HEMA | 9.1 | 8.7 | 8.0 | 8.0 | 7.4 | 7.3 | 7.3 | 7.3 |
| Water | 45.5 | 43.5 | 40.0 | 35.0 | 37.0 | 36.4 | 36.5 | 36.7 |

Examples 6A-6H were evaluated with a Rheological Data Analyzer (RDA) according to the Rheological Test Method described herein. Examples 6D-6H were each found to have a temperature dependant viscosity curve that showed a sharp transition from low viscosity (20,000 to 40,000 Poise (P)) to high viscosity (100,000 to 120,000 P) at temperatures between 28° C. and 38° C. The viscosity versus temperature RDA curves for these examples are shown in FIG. 1. Examples 6A-6C (not shown in FIG. 1) did not show a significant viscosity change between 20° C. and 40° C.

Examples 7A and 7B

TR Viscosity Modifier+Polymerizable Components+Photoinitiator

Example 6H was further modified by the addition of two different photoinitiators. Example 7A was prepared by adding CPQ (0.25%), DPIHFP (1.00%), and EDMAB (1.00%) to Example 6H and Example 7B was prepared by adding IRGACURE 819 (0.50%) to Example 6H.

Figure 2:
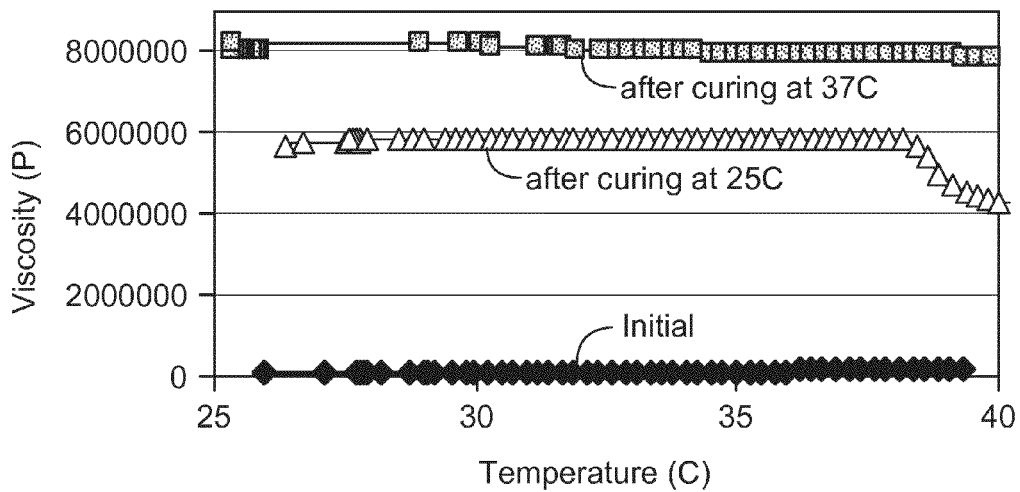
FIG. 2 is an illustration of plots of viscosity (Poise, y-axis) vs. temperature (° C., x-axis) generated using a Rheological Dynamic Analyzer (RDA, Model RDA II) for a composition including a thermally responsive viscosity modifier, polymerizable components, water, and photoinitiator as defined in Example 7A. The plots include the initial state (♦), after curing at 25° C. (▲), and after curing at 37° C. (■).
Figure 3:
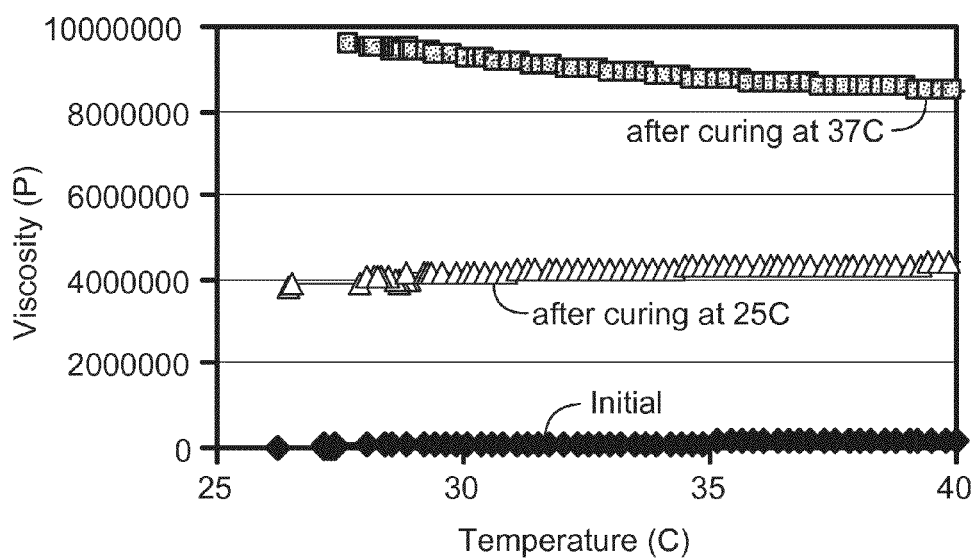
FIG. 3 is an illustration of plots of viscosity (Poise, y-axis) vs. temperature (° C., x-axis) generated using a Rheological Dynamic Analyzer (RDA, Model RDA II) for a composition including a thermally responsive viscosity modifier, polymerizable components, water, and photoinitiator as defined in Example 7B. The plots include the initial state (♦), after curing at 25° C. (▲), and after curing at 37° C. (■).

Examples 7A and 7B were evaluated according to the Rheological Test Method described herein. Evaluations were conducted before and after light exposure for 60 seconds with a dental curing light at either 25° C. (pre-gelled state) or 37° C. (gelled state). Following light exposure, both Examples 7A and 7B cured to hardened materials that were unchanged when cooled back to room temperature. The three viscosity versus temperature RDA curves for Examples 7A and 7B (before light exposure, after light exposure at 25° C., and after light exposure at 37° C.) are shown in FIG. 2 and FIG. 3, respectively. For both Examples 7A and 7B, the test results showed that sample viscosity increased dramatically after light exposure, e.g., to 4 to 6 million P after curing in the pre-gelled state at 25° C. and to 8 to 10 million P after curing in the gelled state at 37° C. Therefore Examples 7A and 7B provide compositions with low viscosity at room temperature, gellation at greater than 30° C., and a non-thermoreversible hardened material state upon light exposure.

Examples 8A-8K

TR Viscosity Modifier+Polymerizable Components

Figure 4:
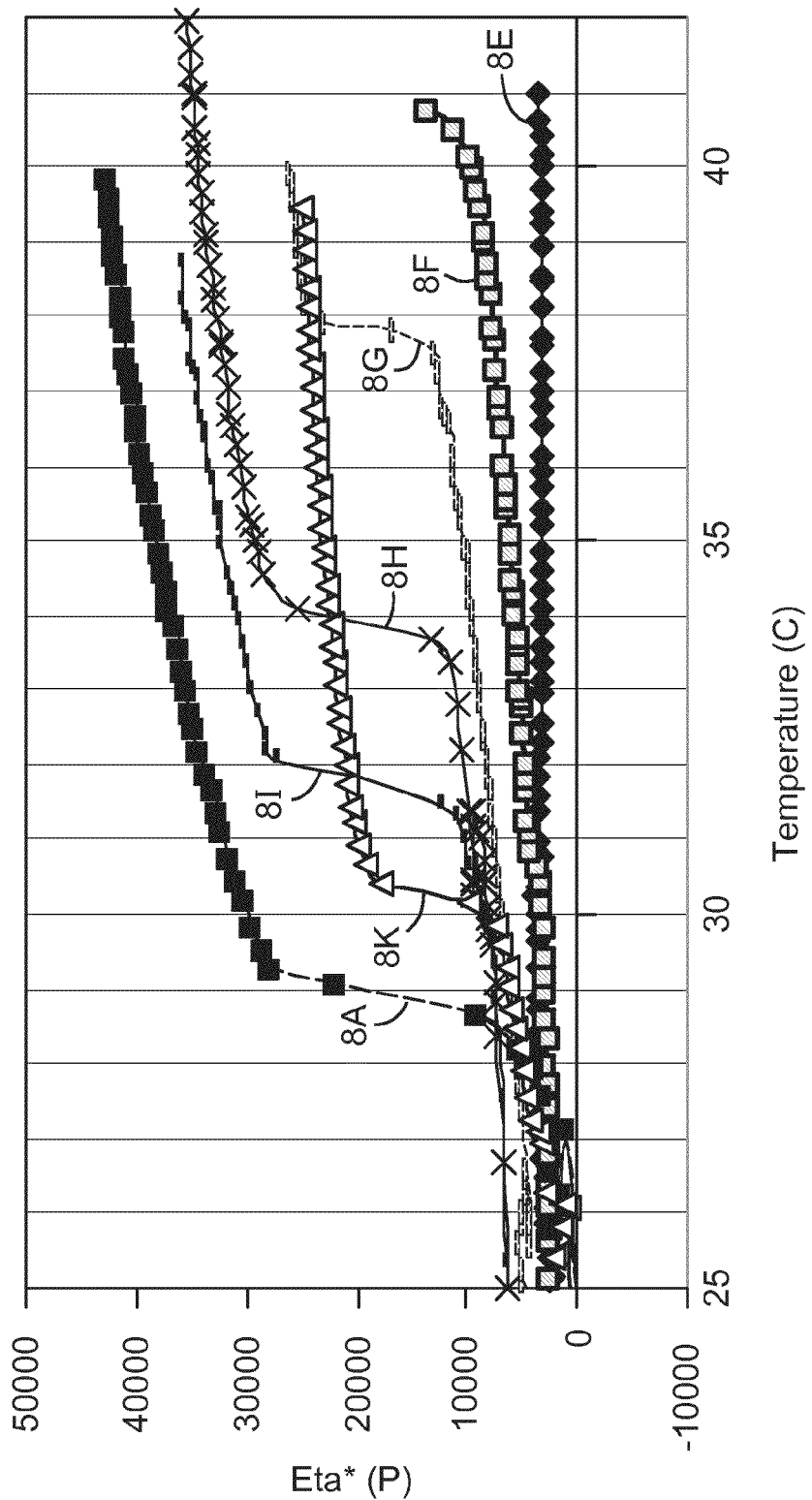
FIG. 4 is an illustration of plots of viscosity (Poise, y-axis) vs. temperature (° C., x-axis) generated using a Rheological Dynamic Analyzer (RDA, Model RDA II) for compositions including thermally responsive viscosity modifiers, polymerizable components, and water as defined in Table 2.

PLURONIC F127 (16.1 parts), IA:ITA:IEM (10.8 parts), PEGDMA 400 (10.8 parts), TEGDMA (2.2 parts), and water (60.2 parts) were transferred to a 250-ml plastic container and thoroughly mixed at room temperature. The resulting solution was designated Example 8A. Examples 8B-8K were prepared in a similar manner with the amounts of individual components shown in Table 2.

described herein. Examples 8A, 8G-8I, and 8K were each found to have a temperature dependant viscosity curve that showed a sharp transition from low viscosity (0 to 12,000 P) to high viscosity (20,000 to 30,000 P) at temperatures between 28° C. and 38° C. Example 8F begin to show a significant increase in viscosity at 41° C. and Example 8E did not show viscosity change in the tested temperature range. The viscosity versus temperature RDA curves for these examples are shown in FIG. 4. Additionally (but not shown in FIG. 4), Examples 8B-8D and 8J did not show a significant viscosity change between 25° C. and 41° C.

Example 9

TR Viscosity Modifier+Polymerizable Components+Photoinitiator

Example 8K was further modified by the addition of the photoinitiator IRGACURE 819 (0.50%) to afford Example 9.

Figure 5:
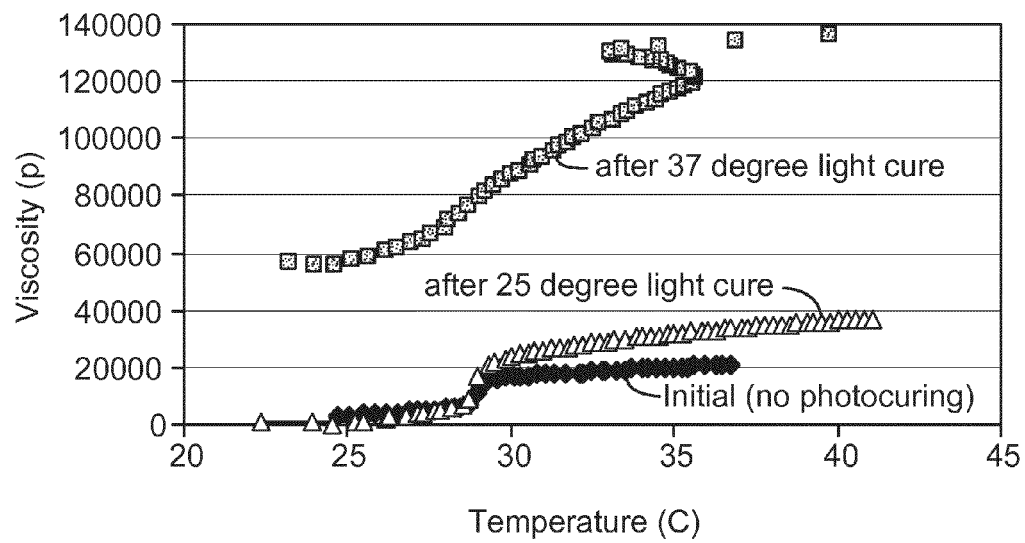
FIG. 5 is an illustration of plots of viscosity (Poise, y-axis) vs. temperature (° C., x-axis) generated using a Rheological Dynamic Analyzer (RDA, Model RDA II) for a composition including a thermally responsive viscosity modifier, polymerizable components, water, and photoinitiator as defined in Example 9. The plots include the initial state (♦), after curing at 25° C. (▲), and after curing at 37° C. (■).

Example 9 was evaluated according to the Rheological Test Method described herein before and after light exposure for 60 seconds with a dental curing light at either 25° C. (pre-gelled state) or 37° C. (gelled state). Following light exposure at 25° C., Example 9 showed only a slight increase in viscosity, whereas at 37° C., viscosity was dramatically increased and the sample cured to a hardened material that was unchanged when cooled back to room temperature. The three viscosity versus temperature RDA curves for Example 9 (before light exposure, after light exposure at 25° C., and after light exposure at 37° C.) are shown in FIG. 5. Therefore, Example 9 provides a composition with low viscosity at room temperature, gellation at greater than 30° C., and a non-thermoreversible hardened material state upon light exposure at an elevated temperature.

Example 10

TR Viscosity Modifier+Polymerizable Components+Redox Initiator System

Example 8K was further modified by the addition of a redox initiator system (i.e., reducing agent and oxidizing agent) that utilized allylthiourea (Sigma-Aldrich) as the reducing agent and sodium persulfate (Sigma-Aldrich) as the oxidizing agent. Specifically, allylthiourea (1.5%) was added to Example 8K to provide Solution A and sodium persulfate (1.0%) was added to Example 8K to provide Solution B. Solutions A and B were then combined in equal portions and mixed to afford Example 10 that was maintained at either 25° C. or 37° C. and then immediately evaluated. It was visually observed that Example 10 at room temperature remained as a

TABLE 2

Component Amounts for Examples 8A-8K

| Component | Amount (Parts) | | | | | | | | | | |
|---|---|---|---|---|---|---|---|---|---|---|---|
| | 8A | 8B | 8C | 8D | 8E | 8F | 8G | 8H | 8I | 8J | 8K |
| Pluronic F127 | 16.1 | 20.4 | 24.3 | 27.8 | 11.4 | 13.3 | 13.7 | 14.8 | 15.5 | 15.3 | 13.3 |
| IA:ITA:IEM | 10.8 | 10.2 | 9.7 | 9.3 | 11.4 | 11.1 | 11.1 | 10.9 | 10.8 | 10.7 | 9.3 |
| PEGDMA 400 | 10.8 | 10.2 | 9.7 | 9.3 | 11.4 | 11.1 | 11.1 | 10.9 | 10.8 | 10.7 | 9.3 |
| TEGDMA | 2.2 | 2.0 | 1.9 | 1.9 | 2.3 | 2.2 | 2.2 | 2.2 | 2.2 | 3.2 | 2.8 |
| Water | 60.2 | 57.1 | 54.4 | 51.9 | 63.6 | 62.2 | 61.9 | 61.1 | 60.7 | 60.0 | 65.3 |

Examples 8A-8K were evaluated with a Rheological Data Analyzer (RDA) according to the Rheological Test Method low-viscosity solution, whereas Example 10 heated to 37° C. immediately transformed into a viscous, immobile gel.

Figure 6:
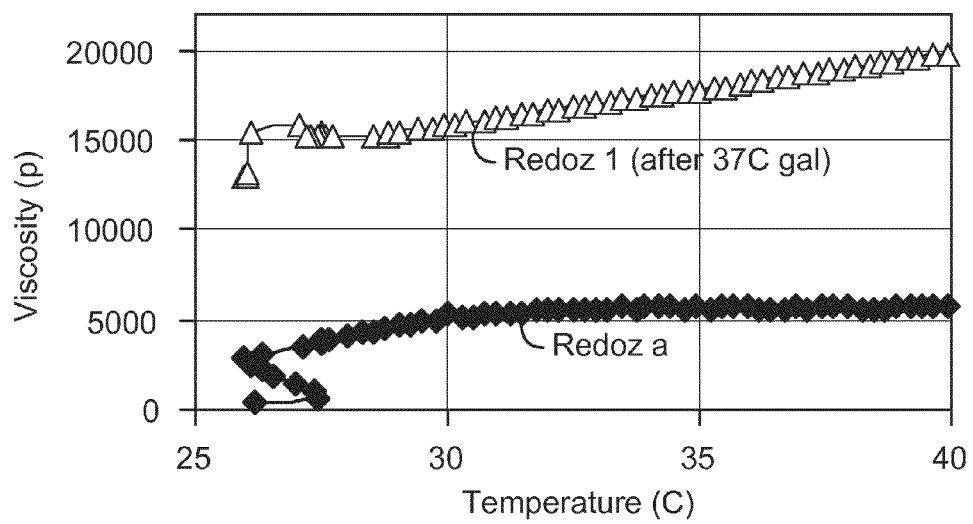
FIG. 6 is an illustration of plots of viscosity (Poise, y-axis) vs. temperature (° C., x-axis) generated using a Rheological Dynamic Analyzer (RDA, Model RDA II) for a composition including a thermally responsive viscosity modifier, polymerizable components, water, and a redox inititiation system as defined in Example 10. The plots include the initial pregelled state at 25° C. (♦) and the gelled state at 37° C. (▲).

Example 10 was evaluated according to the Rheological Test Method described herein at either 25° C. (pre-gelled state) or 37° C. (gelled state). At 25° C., Example 10 did not show a significant increase in viscosity, whereas at 37° C., viscosity was dramatically increased and the sample cured to a hardened material that was unchanged when cooled back to room temperature. The two viscosity versus temperature RDA curves for Example 10 (evaluation at 25° C. and evaluation at 37° C.) are shown in FIG. 6. Therefore, Example 10 provides a composition with low viscosity at room temperature, gellation at greater than 30° C., and a non-thermoreversible hardened material state upon cure with a redox initiation system at an elevated temperature.

Examples 11A-11F

TR Viscosity Modifier+Polymerizable Components

PLURONIC F127 (16.7 parts), PEGDMA 400 (29.2 parts), TEGDMA (4.2 parts), and water (50.0 parts) were transferred to a 250-ml plastic container and thoroughly mixed at room temperature. The resulting solution was designated Example 11A. Examples 11B-11F were prepared in a similar manner with the amounts of individual components shown in Table 3.

TABLE 3

Component Amounts for Examples 11A-11F

| | Amount (Parts) | | | | | |
|---|---|---|---|---|---|---|
| Component | 11A | 11B | 11C | 11D | 11E | 11F |
| Pluronic F127 | 16.7 | 20.0 | 23.1 | 17.4 | 18.4 | 17.9 |
| PEGDMA 400 | 29.2 | 28.0 | 26.9 | 28.9 | 28.6 | 28.7 |
| TEGDMA | 4.2 | 4.0 | 3.8 | 4.1 | 4.1 | 4.1 |
| Water | 50.0 | 48.0 | 46.2 | 49.6 | 49.0 | 49.3 |

Figure 7:
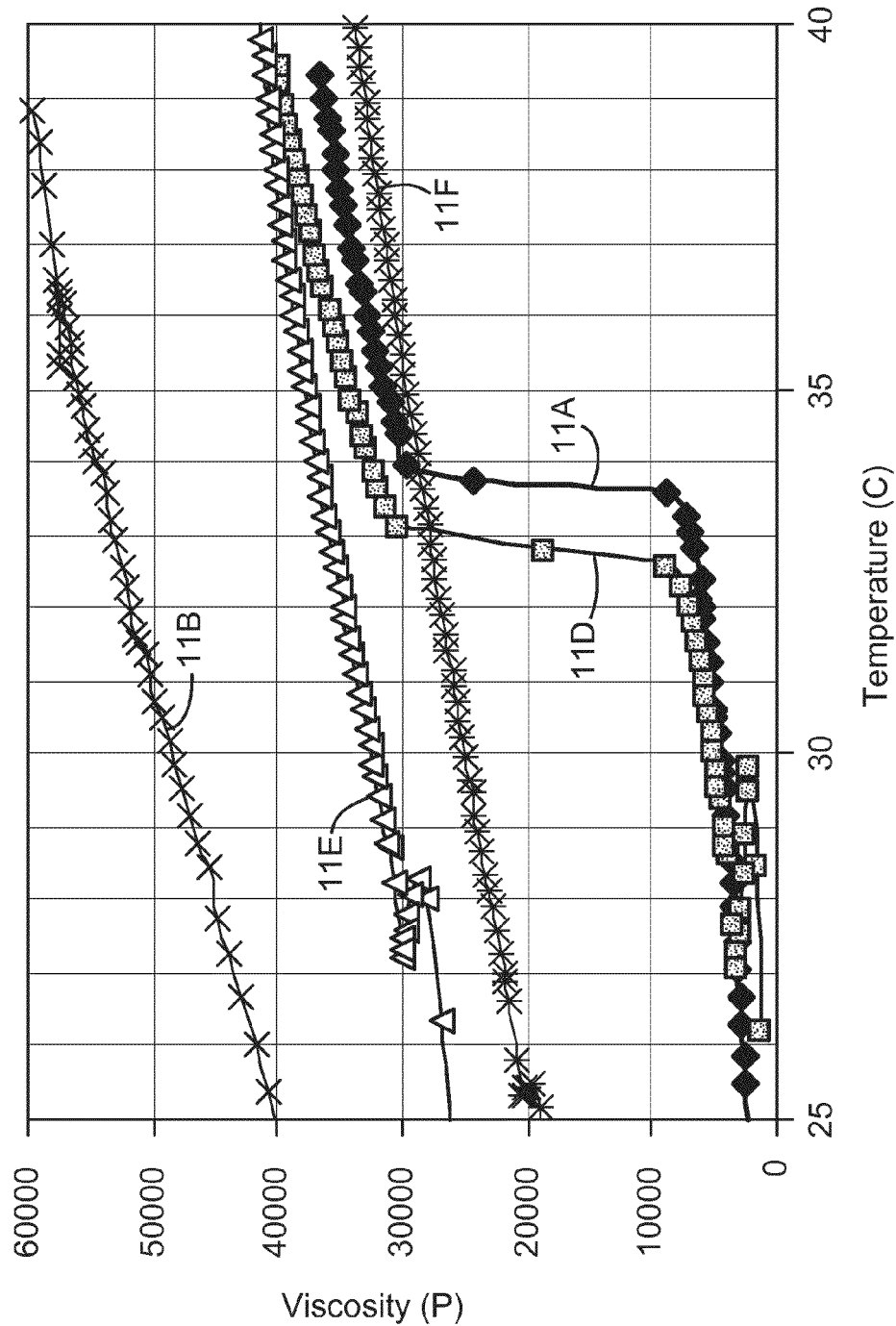
FIG. 7 is an illustration of plots of viscosity (Poise, y-axis) vs. temperature (° C., x-axis) generated using a Rheological Dynamic Analyzer (RDA, Model RDA II) for compositions including thermally responsive viscosity modifiers, polymerizable components, and water as defined in Table 3.

Examples 11A-11F were evaluated with a Rheological Data Analyzer (RDA) according to the Rheological Test Method described herein. Examples 11A and 11D were each found to have a temperature dependant viscosity curve that showed a sharp transition from low viscosity (0 to 10,000 P) to high viscosity (30,000 to 40,000 P) at temperatures between 32° C. and 34° C. Examples 11B, 11E, and 11F were already viscous immobile gels at 25° C. and only showed a slight increase in viscosity with increasing temperature. The viscosity versus temperature RDA curves for these examples are shown in FIG. 7. Additionally (but not shown in FIG. 7), Example 11C did not show a significant viscosity change between 25° C. and 40° C.

Example 12

TR Viscosity Modifier+Polymerizable Components+Photoinitiator

Example 11D was further modified by the addition of the photoinitiator IRGACURE 819 (0.50%) to afford Example 12.

Figure 8:
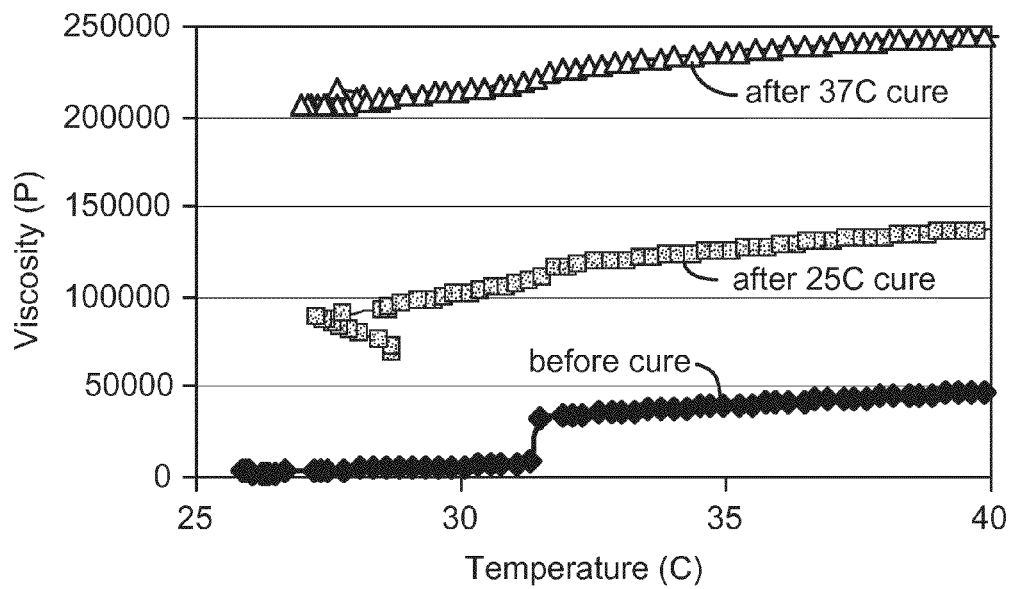
FIG. 8 is an illustration of plots of viscosity (Poise, y-axis) vs. temperature (° C., x-axis) generated using a Rheological Dynamic Analyzer (RDA, Model RDA II) for a composition including a thermally responsive viscosity modifier, polymerizable components, water, and photoinitiator as defined in Example 12. The plots include the initial state (♦), after curing at 25° C. (■), and after curing at 37° C. (▲).

Example 12 was evaluated according to the Rheological Test Method described herein before and after light exposure for 60 seconds with a dental curing light at either 25° C. (pre-gelled state) or 37° C. (gelled state). Following light exposure at 25° C., Example 12 showed a significant increase in viscosity to over 100,000 P, whereas at 37° C., viscosity was even more significantly increased to over 200,000 P. In both cases, the samples cured to hardened materials that were unchanged when cooled back to room temperature. The three viscosity versus temperature RDA curves for Example 12 (before light exposure, after light exposure at 25° C., and after light exposure at 37° C.) are shown in FIG. 8. Therefore, Example 12 provides a composition with low viscosity at room temperature, gellation at greater than 30° C., and a non-thermoreversible hardened material state upon light exposure at an elevated temperature.

Example 13

TR Viscosity Modifier+Polymerizable Components+Redox Initiator System

Example 11D was further modified by the addition of a redox initiator system as described in Example 10. Specifically, allylthiourea (1.5%) was added to Example 11D to provide Solution A and sodium persulfate (1.0%) was added to Example 11D to provide Solution B. Solutions A and B were then combined in equal portions and mixed to afford Example 13 that was maintained at either 25° C. or 37° C. and then immediately evaluated. It was visually observed that Example 13 at room temperature remained as a low-viscosity solution, whereas Example 13 heated to 37° C. immediately transformed into a viscous, immobile gel.

Figure 9:
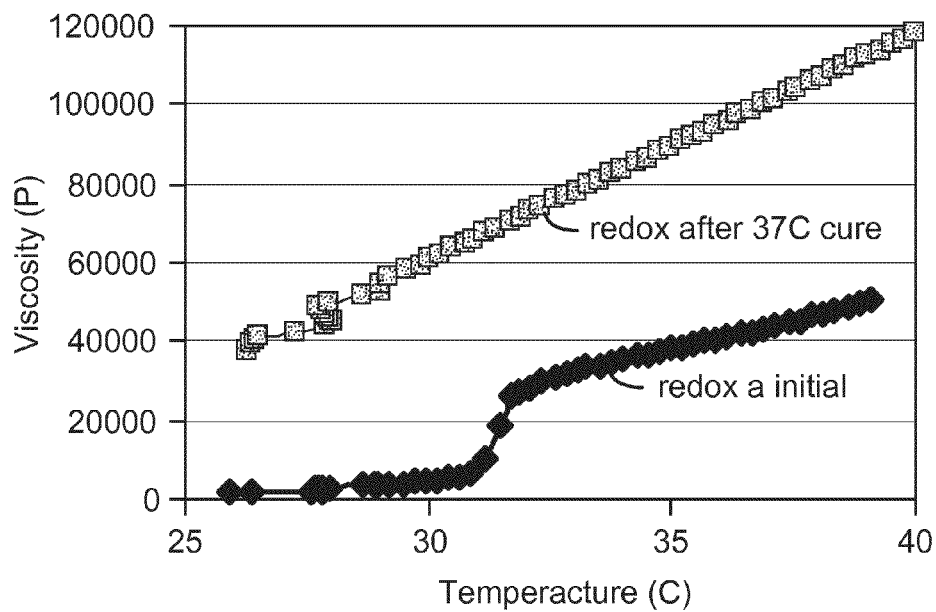
FIG. 9 is an illustration of plots of viscosity (Poise, y-axis) vs. temperature (° C., x-axis) generated using a Rheological Dynamic Analyzer (RDA, Model RDA II) for a composition including a thermally responsive viscosity modifier, polymerizable components, water, and a redox inititiation system as defined in Example 13. The plots include the initial pregelled state at 25° C. (♦) and the gelled state at 37° C. (■).

Example 13 was evaluated according to the Rheological Test Method described herein at either 25° C. (pre-gelled state) or 37° C. (gelled state). At 25° C., Example 13 did not show a significant increase in viscosity, whereas at 37° C., viscosity was dramatically increased and the sample cured to a hardened material that was unchanged when cooled back to room temperature. The two viscosity versus temperature RDA curves for Example 13 (evaluation at 25° C. and evaluation at 37° C.) are shown in FIG. 9. Therefore, Example 13 provides a composition with low viscosity at room temperature, gellation at greater than 30° C., and a non-thermoreversible hardened material state upon cure with a redox initiation system at an elevated temperature.

Examples 14A and 14B

TR Viscosity Modifier+Polymerizable Components+Photoinitiator (Fluoride Release Study)

Hydrogel formulations containing sodium fluoride were evaluated for fluoride release versus time for up to 24 hours. An example utilizing a composition with a gellation temperature of greater than 40° C. (Example 8F) was compared to a composition that gelled at 30° C. (Example 8K). Specifically, samples evaluated according to the Fluoride Release Test Method described herein were Example 14A (Example 8F+0.22% sodium fluoride (Sigma-Aldrich) to afford a composition containing 0.1% (1000 ppm) fluoride ion), Example 14B (Example 8K+0.22% sodium fluoride +0.50% IRGACURE 819 photoinitiator), and Example 14C (Example 14B photocured for 60 seconds at 37° C. with a dental curing light to afford a white immobile gel).

Results from the fluoride release evaluations of Examples 14A, 14B, and 14C are provided in Table 4. The data show that the photocured sample (Example 14C) provided a more controlled fluoride release over time (slower during the first 75 minutes and then a faster release between 75 and 1440 minutes) than the corresponding uncured samples (Examples 14A and 14B).

TABLE 4

Fluoride Release Study

Normalized Fluoride Concentration (ppm) at Designated Times (Minutes)

| Example | 1 | 5 | 10 | 30 | 60 | 75 | 1440 |
|---|---|---|---|---|---|---|---|
| 14A | 8 | 19 | 37 | 52 | 70 | 85 | 117 |
| 14B | 5 | 12 | 21 | 43 | 71 | 84 | 116 |
| 14C | 4 | 10 | 15 | 27 | 40 | 45 | 127 |

Examples 15A-15D

TR Viscosity Modifier+Polymerizable Components+Photoinitiator+FAS Glass

Hybrid glass ionomer compositions containing thermoreversible hydrogel systems with methacrylate functional components and a fluoroalumino silicate (FAS) glass were prepared and evaluated as described below. Each composition either contained PLURONIC F127 or PLURONIC F127 functionalized with IEM (PLURONIC F127-IEM prepared as described in Example 17).

Thermoreversible liquid compositions (Examples 15A and 15B) were prepared by combining the components shown in their relative amounts in Table 5. Liquid aliquots of Examples 15A and 15B were low viscosity solutions at room temperature, but immediately transformed into viscous, immobile gels when heated to 37° C.

TABLE 5

Component Amounts for Examples 15A and 15B

| | Amount (Parts) | |
|---|---|---|
| Component | Example 15A | Example 15B |
| Pluronic F127 | 26.6 | 0 |
| Pluronic F127-IEM | 0 | 26.6 |
| IA:ITA:IEM | 29.4 | 29.4 |
| HEMA | 7.3 | 7.3 |
| CPQ | 0.5 | 0.5 |
| EDMAB | 0.1 | 0.1 |
| DPIHFP | 0.1 | 0.1 |
| Water | 36.7 | 36.7 |

Glass ionomer compositions were prepared by separately combining 1 part of Example 15A or Example 15B with 2.5 parts of FAS-I (an FAS glass prepared as described for FAS V in U.S. patent application Ser. No. 09/916,399) on a paper mixing pad and then mixing the components until homogeneous white pastes (Examples 15C and 15D, respectively) were obtained. Examples 15C and 15D were then irradiated with a dental curing light for 20 seconds at 25° C. to afford hardened materials. The resulting cured resin modified glass ionomer compositions (Examples 15C(cured) and 15D (cured)) were evaluated for diametral tensile strength (DTS) according to the method described herein. Examples 15C (cured) and 15D(cured) had DTS values of 1340±88 psi (9233±606 KPa) and 1560±227 psi (10,748±1564 KPa), respectively.

Examples 16A and 16B

TR Viscosity Modifier+Polymerizable Components+Photoinitiator+FAS Glass

A hybrid glass ionomer composition containing thermoreversible hydrogel systems with methacrylate functional components and a FAS glass was prepared as follows. AA:ITA:IEM (8.90 parts), AA:ITA (3.60 parts), HEMA (4.73 parts), BHT (0.0156 parts), and water (8.23 parts) were combined and thoroughly mixed until a homogeneous solution was obtained. This solution (20 grams) was cooled to 5° C., combined with PLURONIC F127-IEM (2.0 grams), and the resulting composition mixed at 5° C. to afford a homogenous solution that was designated Example 16A.

The glass ionomer composition was prepared by combining Example 16A (10 grams) with FAS-II (25 grams of FAS-I plus 0.2 grams of encapsulated potassium persulfate and 0.12 grams of encapsulated p-sodium toluene sulfinate, the latter encapsulated redox agents prepared as described for U.S. Pat. No. 5,154,762 (Mitra)) on a mixing pad and hand spatulating the components until a homogeneous paste (Example 16B) was obtained. Example 16B was examined for setting time by periodically examining the mixed paste at room temperature with a probe until the flowable paste material transformed into an immobile, hardened solid material. Setting time was 4 minutes.

The hardened material was also evaluated for compressive strength (CS) and diametral tensile strength (DTS) according to the CS and DTS Test Methods described herein and the following results were obtained: CS=28,200±312 psi (194, 298±2150 KPa) and DTS=6050±190 psi (41,684±1309 KPa).

Example 17

Preparation of PLURONIC F127-IEM

PLURONIC F127 (100 parts), tetrahydrofuran (200 parts), and BHT (0.10 parts) were combined in a reaction vessel and mixed until a clear solution was obtained. To the resulting solution was added dibutyltin dilaurate (0.50 parts; Sigma-Aldrich) followed by the addition of IEM (5.0 parts). The resulting mixture was heated to 45° C. and stirred for 2 hours during which time a constant flow of air was run throughout the reaction. The solution was next poured into a large excess of cyclohexane and the resulting white solid precipitate collected by filtration and dried in a 30° C. vacuum oven. NMR spectra analysis confirmed the structure of the solid to be PLURONIC F127 terminated at each end with a 2-methacryloxyethylaminocarboxy moiety ($CH_2$=$C(CH_3)CO_2 CH_2CH_2NHCO_2$—).

Example 18

Preparation of PLURONIC F127-VDMA

PLURONIC F127 (100 parts), tetrahydrofuran (200 parts), and BHT (0.10 parts) were combined in a reaction vessel and mixed until a clear solution was obtained. To the resulting solution was added DBU (0.02 parts; Sigma-Aldrich) followed by the addition of VDMA (0.23 parts). The resulting mixture was heated to 45° C. and stirred for 2 hours during which time a constant flow of air was run throughout the reaction. The solution was next poured into a large excess of cyclohexane and the resulting white solid precipitate collected by filtration and dried in a 30° C. vacuum oven. NMR spectra analysis confirmed the structure of the solid to be PLURONIC F127 terminated at each end with a 2-acrylamidodimethylacetoxy moiety ($CH_2$=$CHCONHC(CH_3)_2 CO_2$—).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of hardening a composition on a surface comprising:
    applying a thermally responsive composition in a low viscosity state at a pre-treatment temperature to the surface, the composition comprising a thermally responsive viscosity modifier selected from the group consisting of a poly(oxyethylene)-poly(oxypropylene) block copolymer and a poly(N-alkyl(meth)acrylamide)polymer; a polymerizable component different than the modifier; and water;
    allowing the composition to warm to a treatment temperature and increase in viscosity to a highly viscous thermally reversible state; and
    inducing the polymerizable component of the composition in the highly viscous thermally reversible state to polymerize and harden the composition, rendering the composition thermally irreversible.

2. The method of claim 1 wherein the surface is the surface of a body.

3. The method of claim 1 wherein the surface is an oral surface.

4. The method of claim 1 wherein inducing polymerization comprises irradiating the composition.

5. The method of claim 1 wherein inducing polymerization comprises irradiating the composition with visible or ultraviolet light.

6. The method of claim 1 wherein inducing polymerization comprises introducing one or more additional components.

7. The method of claim 1 wherein the composition further comprises an initiator.

8. The method of claim 7 wherein the initiator is a photo-initiator.

9. The method of claim 7 wherein the initiator is a free radical inititator.

10. The method of claim 1 wherein the composition further comprises an oxidizing agent and a reducing agent.

11. The method of claim 2 wherein the body is a human body.

12. The method of claim 1 wherein the thermally responsive composition further comprises an additive.

13. The method of claim 12 wherein the additive is selected from the group consisting of fluoride sources, whitening agents, anticaries agents, remineralizing agents, enzymes, breath fresheners, anesthetics, clotting agents, acid neutralizers, chemotherapeutic agents, immune response modifiers, medicaments, indicators, dyes, pigments, wetting agents, surfactants, buffering agents, viscosity modifiers, thixotropes, fillers, polyols, antimicrobial agents, antifungal agents, stabilizers, agents for treating xerostomia, desensitizers, and combinations thereof.

14. The method of claim 12 wherein the additive is a whitening agent selected from the group consisting of a hypochlorite, a peroxide, a peracid, and combinations thereof.

15. The method of claim 1 wherein applying the composition comprises delivering the composition through an orifice.

16. The method of claim 15 wherein the orifice is the orifice of a syringe.

17. The method of claim 1 wherein applying the composition is selected from the group consisting of painting the composition, brushing the composition, syringing the composition, misting the composition, spraying the composition, applying a substrate having the composition thereon, and combinations thereof.

18. The method of claim 1 wherein the thermally responsive composition comprises two or more parts, and wherein applying the composition comprises combining the two or more parts.

19. The method of claim 18 wherein combining comprises using a static mixing device.

20. The method of claim 1 wherein the viscosity of the composition at the treatment temperature, before inducing the polymerizable component to polymerize, is at least 5 times the viscosity of the composition at the pre-treatment temperature.

21. The method of claim 1 wherein the viscosity of the composition at the treatment temperature, after inducing the polymerizable component to polymerize, is at least 10 times the viscosity of the composition at the pre-treatment temperature.

22. The method of claim 1 wherein the pre-treatment temperature is at most room temperature.

23. The method of claim 1 wherein the treatment temperature is body temperature.

24. A method of hardening a composition on an oral surface of a body comprising:
    applying a thermally responsive composition in a low viscosity state at a pre-treatment temperature to the oral surface, the composition comprising a thermally responsive viscosity modifier selected from the group consisting of a poly(oxyethylene)-poly(oxypropylene) block copolymer and a poly(N-alkyl(meth)acrylamide) polymer; a polymerizable component different than the modifier; and water;
    allowing the composition to warm to a treatment temperature and increase in viscosity to a highly viscous thermally reversible state; and
    inducing the polymerizable component of the composition in the highly viscous thermally reversible state to polymerize and harden the composition, rendering the composition thermally irreversible.

25. The method of claim 24 wherein the oral surface is selected from the group consisting of bone, tooth, tongue, gingiva, throat, and combinations thereof.

26. The method of claim 1 wherein the composition comprises at least 5% by weight of the thermally responsive viscosity modifier.

27. The method of claim 14 wherein the peroxide is selected from the group consisting of a hydroperoxide, hydrogen peroxide, carbamide peroxide, and combinations thereof.

* * * * *

UNITED STATES PATENT AND TRADEMARK OFFICE
CERTIFICATE OF CORRECTION

| | | |
|---|---|---|
| PATENT NO. | : 8,900,556 B2 | |
| APPLICATION NO. | : 11/745212 | |
| DATED | : December 2, 2014 | |
| INVENTOR(S) | : Joel Oxman | |

It is certified that error appears in the above-identified patent and that said Letters Patent is hereby corrected as shown below:

On the Title Page

<u>Column 2</u>

Line 1, delete "Polysilxoane" and insert -- Polysiloxane --, therefor.

<u>Column 2</u>

Line 21, delete "Dentrifrice,"" and insert -- Dentifrice," --, therefor.

In the Drawings

<u>Sheet 4 of 6 (FIG. 6)</u>

Line 2, delete "Redoz" and insert -- Redox --, therefor.

<u>Sheet 4 of 6 (FIG. 6)</u>

Line 4, delete "Redoz" and insert -- Redox --, therefor.

In the Specification

<u>Column 3</u>

Line 48, delete "inititiation" and insert -- initiation --, therefor.

<u>Column 3</u>

Line 67, delete "inititiation" and insert -- initiation --, therefor.

Signed and Sealed this
Twenty-second Day of September, 2015

Michelle K. Lee
*Director of the United States Patent and Trademark Office*

CERTIFICATE OF CORRECTION (continued)
U.S. Pat. No. 8,900,556 B2

Column 8

Line 57, delete "theramlly" and insert -- thermally --, therefor.

Column 9

Line 27, delete "2-isocyantoethyl" and insert -- 2-isocyanatoethyl --, therefor.

Column 13

Line 19, delete "theological" and insert -- rheological --, therefor.

Column 14

Line 23 (approx.), delete "Terrytown," and insert -- Tarrytown, --, therefor.

In the Claims

Column 23

Line 44, In Claim 9, delete "inititator." and insert -- initiator. --, therefor.